US00PP19013P3

(12) United States Plant Patent
Yencho et al.

(10) Patent No.: US PP19,013 P3
(45) Date of Patent: Jul. 15, 2008

(54) ORNAMENTAL SWEETPOTATO PLANT NAMED 'SWEET CAROLINE SWEETHEART RED'

(50) Latin Name: *Ipomoea batatas*
Varietal Denomination: Sweet Caroline Sweetheart Red

(75) Inventors: George Craig Yencho, Raleigh, NC (US); Kenneth Pecota, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 101 days.

(21) Appl. No.: 11/394,941

(22) Filed: Mar. 31, 2006

(65) Prior Publication Data

US 2007/0143894 P1 Jun. 21, 2007

Related U.S. Application Data

(60) Provisional application No. 60/752,486, filed on Dec. 21, 2005.

(51) Int. Cl.
*A01H 5/00* (2006.01)

(52) U.S. Cl. ..... Plt./258

(58) Field of Classification Search ..... Plt./258
See application file for complete search history.

(56) References Cited

U.S. PATENT DOCUMENTS

2007/0143894 P1 * 6/2007 Yencho et al. ..... Plt./258

* cited by examiner

*Primary Examiner*—Wendy C. Haas
*Assistant Examiner*—Georgia Helmer
(74) *Attorney, Agent, or Firm*—Myers Bigel Sibley & Sajovec P.A.

(57) ABSTRACT

*Ipomoea batatas* 'Sweet Caroline Sweetheart Red' is a moderately compact cultivar producing many shoots and having dense foliage. This cultivar is distinguishable from other cultivars by its small to medium-sized, heart-shaped, red-purple to red-bronze colored leaves. The plant has good vigor, but is less vigorous than *Ipomoea batatas* 'Margarita' and 'Blackie', and unlike these cultivars, 'Sweet Caroline Sweetheart Red' may be grown in containers with other species. The production of flowers by 'Sweet Caroline Sweetheart Red' is relatively rare even under short day conditions.

2 Drawing Sheets

Latin name of the genus and species: The Latin name of the novel, ornamental plant variety disclosed herein is *Ipomoea batatas* (L.) Lam.

Variety denomination: The inventive cultivar of *Ipomoea batatas* disclosed herein has been given the varietal denomination 'Sweet Caroline Sweetheart Red'.

BACKGROUND OF THE INVENTION

*Ipomoea* species are members of the morning glory family Convolvulaceae. *Ipomoea batatas,* the cultivated species, is commonly produced for consumption and referred to as the white or yellow sweetpotato and the orange yam. The plants are typically fast growing, green vines possessing a wide variety of leaf shapes ranging from palmate and deeply lobed, to cordate or triangular shaped leaves with no lobes. Ornamental sweetpotatoes, which have been bred and selected for their unique foliage colors, leaf shapes and plant habits, typically do not produce large fleshy storage roots like the sweetpotato cultivated for consumption. In comparison, storage roots produced by ornamental sweetpotatoes are typically not as large because no selection has been exercised for yield, thus storage roots do not begin to swell until very late in the season. Further, the few storage roots that are formed by ornamental sweetpotatoes are typically not as attractive as those produced by the tablestock types as they are generally cracked, very malformed, often mottled in skin and flesh color, and are not palatable.

Late in the growing season when day-lengths begin to shorten or when the plants are stressed, ornamental sweetpotato plants produce tubular flowers that are similar to morning glories, but most plantings are dominated by the appearance of the foliage. The plants are highly desirable due to their ability to grow under varied stress conditions, cover a large space, and last the entire growing season. Moreover, these plants have few insect or disease problems.

Until the release of the Sweet Caroline series of ornamental sweet potatoes (see below) there were six popular types of *Ipomoea batatas* ornamental sweetpotatoes being cultivated primarily for their annual, summer vines in landscaping applications. These six cultivars are: 'Blackie' (not patented), having purple foliage and lavender flowers; 'Terrace Lime' (not patented) and 'Margarita' (not patented; also known as 'Sulfur'), which have large brilliant chartreuse leaves and lavender blooms; 'Black Heart' (not patented; also known as 'Ace of Spades'), having heart-shaped leaves with burgundy purple color; 'Tricolor' (not patented; also known as 'Pink Frost'), a variegated plant having pale green, white, and pink-margined leaves; and 'Lady Fingers' (unpatented), which has medium green, dainty leaves divided into long, thin, fingerlike lobes that are complemented by burgundy stems and veins.

*Ipomoea batatas* 'Margarita' was recently released in the United States, and has become widely used as a landscape annual. However, it is not suitable for mixed containers as their variety exhibits a very vigorous growth and tends to out-compete other species. See Armitage, A. M. and J. M. Garner, (2001) *Ipomoea batatas* 'Margarita'. Hort Science 36:178. Another popular variety, 'Blackie', is a vigorous purple-leaved clone, which is also unsuited to containerized gardens.

Therefore, to meet the current horticultural demand, it is desirable to produce new, more robust cultivars of ornamental sweetpotato with attractive foliage colors, leaf shapes, and plant architectures. In addition, it would be advantageous to develop cultivars or ornamental sweetpotato exhibiting a more compact growth, and which do not out-compete other species in mixed containers.

*Ipomoea batatas* 'Sweet Caroline Light Green' (U.S. Pat. No. PP15,028, issued Jul. 20, 2004), 'Sweet Caroline Green' (U.S. Pat. No. PP15,056, issued Aug. 3, 2004), 'Sweet Caroline Bronze' (U.S. Pat. No. PP15,437, issued Dec. 21, 2004), 'Sweet Caroline Purple' (U.S. Pat. No. PP14,912, issued Jun. 15, 2004), and 'Sweet Caroline Red' (U.S. Pat. No. PP17,483 issued Mar. 13, 2007) are recently introduced cultivars developed North Carolina State University that are characterized by compact growth habit, moderate to deeply lobed palmate leaves, and attractive foliage color.

The present invention relates to a new and distinct variety of *Ipomoea batatas* named 'Sweet Caroline Sweetheart Red'. 'Sweet Caroline Sweetheart Red' is a moderately-compact variety producing many shoots and having dense foliage. This variety is distinguishable from other varieties by its small to medium-sized, heart-shaped, red-purple to red-bronze colored leaves. The plant has good vigor, but is less vigorous than 'Margarita' and 'Blackie' and, unlike these varieties, 'Sweet Caroline Sweetheart Red' may be grown in containers with other species.

Lineage. The *Ipomoea batatas* 'Sweet Caroline Sweetheart Red' cultivar (breeding designation NC848-6ORN) originated from a conventional cross between *Ipomoea batatas* cultivars NC136-1ORN (the female parent; not patented) and NC146-1ORN (the male parent; not patented) conducted from October 2002 to April 2003 at Raleigh, N.C.

NC136-1ORN resulted from a cross between 'Sulfur' (the female parent) and the clone 'S×BL R5-18' (the male parent; not patented). 'S×BL R5-18' was derived from a cross between 'Sulfur' (the female parent)×'Blackie' (the male parent). NC146-1ORN resulted from a cross between 'Sulfur' and the clone 'S×BLR7-2', which was derived from a cross between 'Sulfur' (the female parent)×'Blackie' (the male parent). Seed from this cross were planted in Raleigh, N.C. in Spring 2003. The single, individual plant now known as *Ipomoea batatas* 'Sweet Caroline Sweetheart Red' was selected in August and September 2003 because of its combination of exceptional features, and has been propagated asexually since that time.

Asexual Reproduction. Since its selection, *Ipomoea batatas* 'Sweet Caroline Sweetheart Red' has been asexually reproduced at Raleigh, N.C., predominantly by vegetative propagation of vine cuttings. Successively, there have been two cycles of vegetative propagation, one cycle of tissue culture micropropagation, and multiple vegetative propagation cycles to increase the plant population. Asexual reproduction of the new Ornamental Sweetpotato cultivar by cuttings has shown that the unique features of the new cultivar are stable and the plant reproduces true to type in successive generations of asexual reproduction.

SUMMARY OF THE INVENTION

*Ipomoea batatas* 'Sweet Caroline Sweetheart Red' is a moderately compact cultivar producing many shoots and having dense foliage. This cultivar is distinguishable from other cultivars by its small to medium-sized, heart-shaped, red-purple to red-bronze colored leaves. The plant has good vigor, but is less vigorous than *Ipomoea batatas* 'Margarita' and 'Blackie', and unlike these cultivars, 'Sweet Caroline Sweetheart Red' may be grown in containers with other species. The production of flowers by 'Sweet Caroline Sweetheart Red' is relatively rare even under short day conditions.

BRIEF DESCRIPTION OF THE DRAWINGS

The photographs in the drawings were made using conventional techniques and show the colors as true as reasonably possible by conventional photography. Colors in the photographs may differ slightly from the color values cited in the detailed botanical description, which accurately describe the colors of the new *Ipomoea batatas*.

DETAILED BOTANICAL DESCRIPTION

Figure 1:
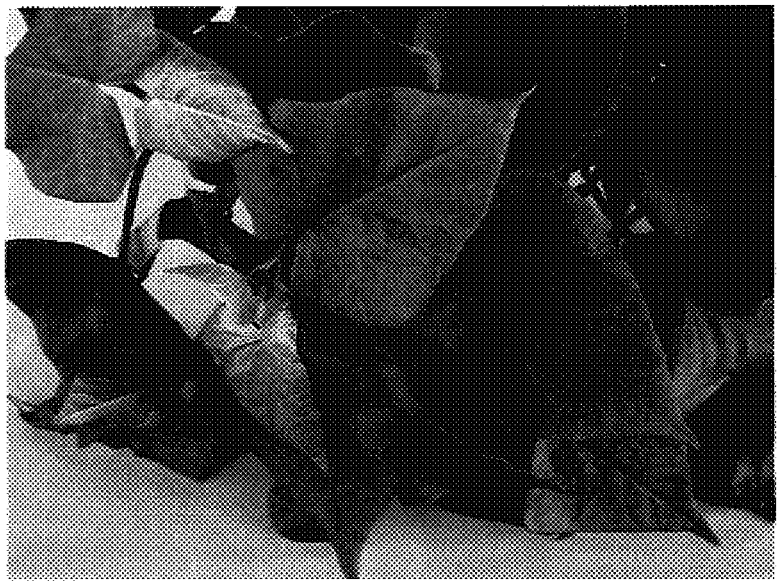
FIG. 1 is a color photograph showing both new and mature foliage produced by *Ipomoea batatas* 'Sweet Caroline Sweetheart Red'. The plant shown in FIG. 1 is 11 weeks of age.
Figure 2:
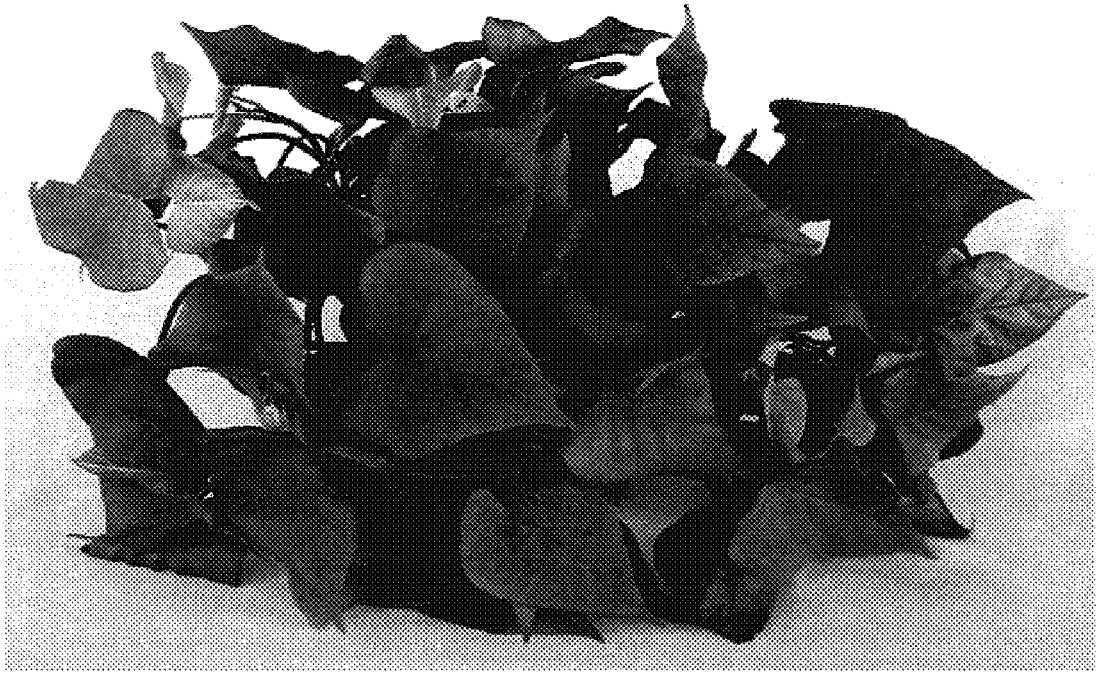
FIG. 2 is a color photograph of a typical plant of the *Ipomoea batatas* 'Sweet Caroline Sweetheart Red'. The plant shown in FIG. 2 is 11 weeks of age.

The following is a detailed description of the botanical characteristics of the new and distinct cultivar of *Ipomoea batatas* plant known by the denomination 'Sweet Caroline Sweetheart Red'. All colors cited herein refer to The Royal Horticultural Society Colour Chart (The Royal Horticultural Society, London, 1995 edition) designations except where general terms of ordinary dictionary significance are used. Where dimensions, sizes, colors, and other characteristics are given, it is to be understood that such characteristics are approximations or averages set forth as accurately as practicable.

The descriptions reported herein are from 11-week-old specimens. *Ipomoea batatas* 'Sweet Caroline Sweetheart Red' has not been observed under all possible environmental conditions; therefore, the phenotype may vary somewhat with variations in the environment such as season, temperature, light intensity, day length, cultural conditions, and the like, without however any variance in the genotype.

Technical Description of the Variety.

Above-ground structure. *Ipomoea batatas* 'Sweet Caroline Sweetheart Red' is an oval, mounding plant. Plant height is 17 cm and its area of spread is 44×54 cm. It is a fast grower with good vigor. Foliage is very dense but not as compact and slightly more vining than *Ipomoea batatas* 'Sweet Caroline Sweetheart Light Green' (U.S. Plant patent application 20070143896 published Jun. 21, 2007).

Branching habitat. Very free branching with no basal shoots.

Lateral shoots. The number of lateral shoots varies but averages around 5 with short secondary shoots. Lateral branch length: about 47 cm. Diameter: about 0.45 cm. Internode length: about 2.3 cm. Stems are round a little coarse with a few scattered hairs; however, the stems are not truly pubescent. The shoots are initially upright but then fall outward and tend to grow outward. Color: greyed-burgundy (RHS 187B).

Petiole. Leaf petiole length varies with an average of 7 cm. Diameter: 0.3 cm. Petiole texture is smooth. Color is darker than 186A, above and below.

Foliage. Leaves are alternate and tend to spiral around the stems. They are simple and heart-shaped (cordate), smooth and mat with no pubescence. The number of leaves per stem varies with length but an average stem has about 15 leaves. The leaf is acuminate and the base is cordate. Leaf margins are entire to slightly lobed. Leaf length averages 10 cm (up to 12 cm) and leaf width averages 7.8 cm (up to 9.5 cm). The venation pattern is palmate at the leaf base becoming arcuate toward the leaf tip. Young leaves emerge a bright yellow-green color. As they mature, the leaves develop anthocyanin pigment turning a red-purple to red-bronze in color: Color: see Table 1.

TABLE 1

| Leaf Structure | Upper Surface | Lower Surface |
|---|---|---|
| Young Leaf | Bright yellow-green, RHS 144 | Bright yellow-green, RHS 144 |
| Mature Leaf | Greyed-purple, a little more grey than RHS 187A | Greyed-purple, a little darker than RHS 186A |
| Vein | RHS 187A | RHS 187D |

Flowers. 'Sweet Caroline Sweetheart Red' does not flower well, even under short day conditions. The precise photoperiod for flower induction is currently unknown. Plants may also flower sporadically throughout the season in response to a variety of stressful conditions (e.g., drought, nutrient stress, cloudy weather). It is noted that not only if flowering in this variety rare, but also, when flowers are produced, they are ephemeral (in most cases open only in the morning).

The inflorescence is generally a cyme in which there is one solitary peduncle. Peduncles (59B) are red, averaging 65 mm long from mature leaf axils with an average diameter of 3 mm. Usually buds of the first and second order are developed, but often, single flowers are produced. Buds are rose colored (186B and 186C) and around 20 mm in length and 5 mm in diameter 24 hours before opening.

The corolla is composed of five fused petals that form a funnel with a pentagonal limb. Corolla width: ~3.4 cm. corolla length: ~4.5 cm. The corolla has no fragrance. The limb color is very pale lavender, while the outer throat color is lavender and the inner throat color is purple. Inner limb color: 69D, Outer limb color: 69B, Inner throat color: N80B, Outer throat color: 77D. There are five sepals, with an average length of 8.3 mm and width of 3.7 mm. The sepals have an oblong apex and are purple in color. Outer sepal color: 59B. Inner sepal color: 59C.

Each flower has one pistil with a light cream-colored style (157C). The stigma is cream colored (157A) and the style averages about 2 mm wide and 22 mm long. The stigma is exerted relative to the stamens. The ovary is yellow (1C) and superior with two locules that contain one or two ovules. Orange basal glands (163A) containing nectar continuing halfway up the ovary are at the base of the ovary. There are five cream colored anthers (158D) that are approximately 3 mm long. Pollen (158D) is profuse. True seed can be obtained via compatible crosses. There is some variation in flower size and color, depending on the environmental conditions. Descriptions are based on: CIP, AVRDC, IBPGR. 1991. Descriptors for Sweet Potato. Huaman, Z., editor. International board for Plant Genetic Resources, Rome, Italy.

Figure 3:
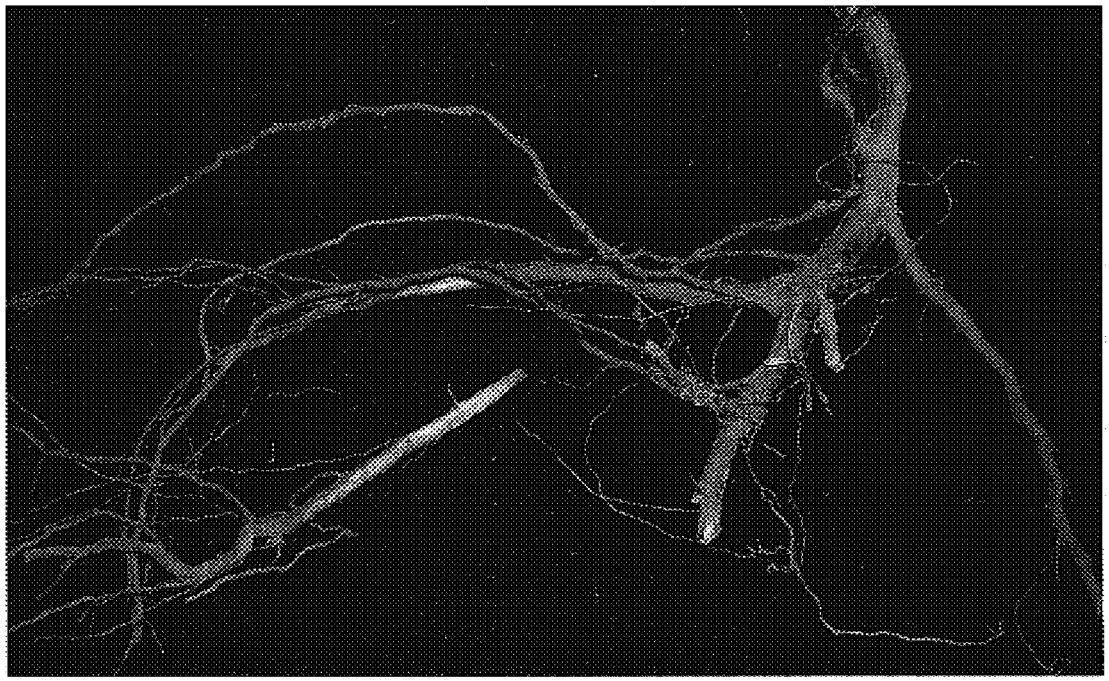
FIG. 3 is a color photograph showing typical storage roots produced by *Ipomoea batatas* 'Sweet Caroline Sweetheart Red' 123 days after planting. Plants were planted as five-hill plots spaced 30.5 cm apart in the row at the Horticultural Crops Research Station, Clinton, N.C. USA.

Below-ground structure. Plants form no, to very small, underground storage roots that are highly malformed and do not meet USDA Sweetpotato Storage Root Grade Standards (FIG. 3). Storage roots that do form typically possess deep rose colored skin (187D) with a cream colored flesh (161D).

Growth conditions. *Ipomoea batatas* 'Sweet Caroline Sweetheart Red' has good vigor, a moderately fast growth rate, and is very adaptable to container culture. In locales with mild winter conditions, *Ipomoea batatas* 'Sweet Caroline Sweetheart Red' will grow perennially; otherwise it is an annual plant. Similar to cultivated sweetpotatoes, wind or rain rarely causes much damage to 'Sweet Caroline Sweetheart Red', but if damage does occur, the plant drops the damaged leaves and grows new shoots at nodes where the leaves were lost.

Disease or pest resistance. 'Sweet Caroline Sweetheart Red' is susceptible to Sweetpotato Feathery Mottle Virus and damage by Japanese beetles.

Comparison with other *Ipomoea batatas* Cultivars.

'Sweet Caroline Sweetheart Red' is very distinct based on leaf color, leaf shape and plant architecture (Table 2). Of the six most common cultivars of ornamental sweetpotato, *Ipomoea batatas* 'Sweet Caroline Sweetheart Red' is best compared with 'Black Heart' (unpatented;) and 'Sweet Caroline Bronze' U.S. Plant Pat. No. 15,437, issued Dec. 21, 2004. 'Black Heart' has medium to large-sized spade- to heart-shaped leaves with burgundy purple color. 'Sweet Caroline Bronze' has bronze to reddish-bronze, deeply lobed leaves; whereas, 'Sweet Caroline Sweetheart Red' possesses small to medium-sized heart- to spade-shaped leaves that are red-purple to red-bronze in color. 'Sweet Caroline Sweetheart Red' exhibits a moderately compact growth habit, as does 'Sweet Caroline Bronze', while 'Black Heart' has a trailing habit. 'Sweet Caroline Sweetheart Red' is highly branched resulting in a more bunched and fuller appearance, which is more suitable for containerized propagation, as compared to 'Black Heart'.

The parental strains used to produce 'Sweet Caroline Sweetheart Red' were NC136-1ORN (female parent) and NC146-1ORN (male parent). NC136-1ORN is a highly vigorous, moderately trailing, and moderately branched plant with large heat-shaped to slightly lobed leaves that are greenish-bronze in color. NC146-1ORN is a moderately vigorous, trailing, and moderately branched plant with medium sized heart-shaped leaves that are greenish-bronze in color.

TABLE 2

| Characteristic | New Variety 'Sweet Caroline Sweetheart Red' | Comparison 1 'Sweet Caroline Bronze' | Comparison 2 'Black Heart' |
|---|---|---|---|
| Plant Habit | Moderately Compact | Moderately Compact | Trailing |
| Foliage Color | Red-Purple to Red-Bronze | Red to Reddish Bronze | Purple |
| Leaf Size | Moderate | Moderate | Moderate to Large |
| Leaf Shape | Heart-Shaped to Spade-Shaped | Deeply Lobed | Heart-Shaped to Spade-Shaped |

What is claimed is:

1. A new and distinct cultivar of *Ipomoea batatas* plant named 'Sweet Caroline Sweetheart Red', substantially as illustrated and described herein.

* * * * *

UNITED STATES PATENT AND TRADEMARK OFFICE

CERTIFICATE OF CORRECTION

PATENT NO. : PP 19,013 P3
APPLICATION NO. : 11/394941
DATED : July 15, 2008
INVENTOR(S) : Yencho et al.

It is certified that error appears in the above-identified patent and that said Letters Patent is hereby corrected as shown below:

Column 3, Paragraph 5, Lines 4 and 7:
Please correct "(the female parent)x'Blackie'"
To read -- (the female parent) x 'Blackie' --

Column 4, Under "Detailed Botanical Description", Paragraph 4 beginning "Lateral Shoots", Line 4: Please correct "Stems are round a little coarse"
To read -- Stems are round and a little coarse --

Column 5, Line 8: Please correct "The leaf is acuminate"
To read -- The leaf tip is acuminate --

Column 5, Paragraph beginning with "Flowers", Line 6:
Please correct "not only if"
To read -- not only is --

Signed and Sealed this

Fourteenth Day of October, 2008

JON W. DUDAS
*Director of the United States Patent and Trademark Office*